United States Patent
Lee et al.

(10) Patent No.: US 9,291,539 B2
(45) Date of Patent: Mar. 22, 2016

(54) DOWNHOLE REBOUND HARDNESS MEASUREMENT WHILE DRILLING OR WIRELINE LOGGING

(75) Inventors: Ji Soo Lee, Houston, TX (US); Terrance H. Quinn, The Woodlands, TX (US); David A. Curry, Askett (GB); Javier A. Franquet, Spring, TX (US); Christopher A. Wolfe, Katy, TX (US); Michael M. Reese, Youngsville, LA (US)

(73) Assignee: BAKER HUGHES INCORPORATED, Houston, TX (US)

( * ) Notice: Subject to any disclaimer, the term of this patent is extended or adjusted under 35 U.S.C. 154(b) by 646 days.

(21) Appl. No.: 13/050,660

(22) Filed: Mar. 17, 2011

(65) Prior Publication Data
US 2012/0234600 A1 Sep. 20, 2012

(51) Int. Cl.
*E21B 49/00* (2006.01)
*G01N 3/52* (2006.01)

(52) U.S. Cl.
CPC .............. *G01N 3/52* (2013.01); *E21B 49/006* (2013.01)

(58) Field of Classification Search
USPC .................. 166/250.01, 254.2; 175/40, 50; 73/152.03
See application file for complete search history.

(56) References Cited

U.S. PATENT DOCUMENTS

| | | | |
|---|---|---|---|
| 4,599,904 A * | 7/1986 | Fontenot | 73/783 |
| 4,813,278 A | 3/1989 | Kosugi | |
| 5,226,310 A | 7/1993 | Steiger | |
| 5,720,354 A | 2/1998 | Stump et al. | |
| 5,904,210 A | 5/1999 | Stump et al. | |
| 6,161,630 A | 12/2000 | Stump et al. | |
| 6,308,787 B1 | 10/2001 | Alft | |
| 6,315,062 B1 | 11/2001 | Alft et al. | |
| 6,324,904 B1 | 12/2001 | Ishikawa et al. | |
| 6,435,286 B1 | 8/2002 | Stump et al. | |
| 6,470,976 B2 * | 10/2002 | Alft et al. | 175/61 |
| 6,484,818 B2 | 11/2002 | Alft et al. | |
| 6,714,873 B2 | 3/2004 | Bakulin et al. | |
| 6,719,069 B2 | 4/2004 | Alft et al. | |
| 6,755,263 B2 | 6/2004 | Alft et al. | |
| 6,829,947 B2 | 12/2004 | Han et al. | |
| 6,886,644 B2 | 5/2005 | Stump et al. | |
| 6,938,458 B2 | 9/2005 | Han et al. | |
| 7,103,982 B2 * | 9/2006 | Haugland | 33/304 |

(Continued)

FOREIGN PATENT DOCUMENTS

| | | |
|---|---|---|
| EP | 1635034 A1 | 3/2006 |
| WO | WO2008086463 A1 | 7/2008 |
| WO | WO2009029269 A2 | 3/2009 |

OTHER PUBLICATIONS

Aydin et al., The Schmidt hammer in rock material characterization, Aug. 22, 2005, Engineering Geology 81, 1-14.*

*Primary Examiner* — David Andrews
(74) *Attorney, Agent, or Firm* — Cantor Colburn LLP

(57) ABSTRACT

A method and apparatus for estimating a rock strength profile of a formation is disclosed. A tool having a testing surface is conveyed into a wellbore in the formation. The testing surface is propelled to impact the formation at a plurality of depths in the wellbore. A measurement of hardness of the formation is obtained from a rebound of the testing surface from the formation at the plurality of depths. The rock strength profile of the formation is estimated using the obtained measurements of hardness at the plurality of depths. A parameter for drilling the wellbore can be affected using the estimated rock strength profile.

17 Claims, 5 Drawing Sheets

(56) References Cited

U.S. PATENT DOCUMENTS

| | | |
|---|---|---|
| 7,143,844 B2 | 12/2006 | Alft et al. |
| 7,182,151 B2 | 2/2007 | Stump et al. |
| 7,289,871 B2 | 10/2007 | Williams |
| 7,555,414 B2 | 6/2009 | Calhoun et al. |
| 7,607,494 B2 | 10/2009 | Alft et al. |
| 2004/0118199 A1 | 6/2004 | Frost et al. |
| 2008/0053705 A1 | 3/2008 | Aronstam et al. |

* cited by examiner

US 9,291,539 B2

DOWNHOLE REBOUND HARDNESS MEASUREMENT WHILE DRILLING OR WIRELINE LOGGING

BACKGROUND OF THE DISCLOSURE

1. Field of the Disclosure

The present disclosure is related to methods and apparatus for estimating a rock strength profile of a wellbore formation in-situ.

2. Description of the Related Art

In petroleum exploration, drilling a wellbore or borehole in an earth formation employs a drill string with a drill bit at an end of the drill string. The speed and effectiveness of drilling is determined in part on the type of rock that is being drilled and its hardness or strength. Various types of rock that can be drilled can range from hard rocks such as granites and dolomites to soft rocks such as sandstones and shales. Various devices for estimating rock hardness are known in the art. However, these require obtaining a core sample and retrieving the sample to a surface location for testing, which can be time-consuming and expensive. Therefore, the present disclosure provides a method and apparatus for estimating in-situ a rock strength profile of a formation.

SUMMARY OF THE DISCLOSURE

In one aspect, the present disclosure provides a method of estimating a rock strength profile of a formation, the method including: conveying a tool having a testing surface into a wellbore in the formation; propelling the testing surface to impact the formation at a plurality of depths in the wellbore; obtaining a measurement of hardness of the formation from a rebound of the testing surface from the formation at the plurality of depths; and estimating the rock strength profile of the formation using the obtained measurements of hardness at the plurality of depths.

In another aspect, the present disclosure provides a method of drilling a wellbore, the method including: conveying a tool having a testing surface into a wellbore in the formation; propelling the testing surface to impact the formation at a plurality of depths in the wellbore; obtaining a measurement of hardness of the formation from a rebound of the testing surface from the formation at the plurality of depths; estimating the rock strength profile of the formation using the obtained measurements of hardness at the plurality of depths; and affecting a parameter for drilling the wellbore using the estimated rock strength profile.

In another aspect, the present disclosure provides an apparatus for estimating a rock strength profile of a formation, comprising: a tool configured to be conveyed into the wellbore; a testing surface disposed on the tool configured to propel against the formation at a plurality of depths in the wellbore and rebound from the formation as a result of the impact; and a processor configured to: obtain a measurement of hardness of the formation from a rebound of the testing surface from the formation at the plurality of depths, and estimate the rock strength profile of the formation from the obtained measurements of hardness at the plurality of depths.

Examples of certain features of the apparatus and method disclosed herein are summarized rather broadly in order that the detailed description thereof that follows can be better understood. There are, of course, additional features of the apparatus and method disclosed hereinafter that will form the subject of the claims.

BRIEF DESCRIPTION OF THE DRAWINGS

For detailed understanding of the present disclosure, references should be made to the following detailed description, taken in conjunction with the accompanying drawings, in which like elements have been given like numerals and wherein.

DETAILED DESCRIPTION OF THE DISCLOSURE

Figure 1:
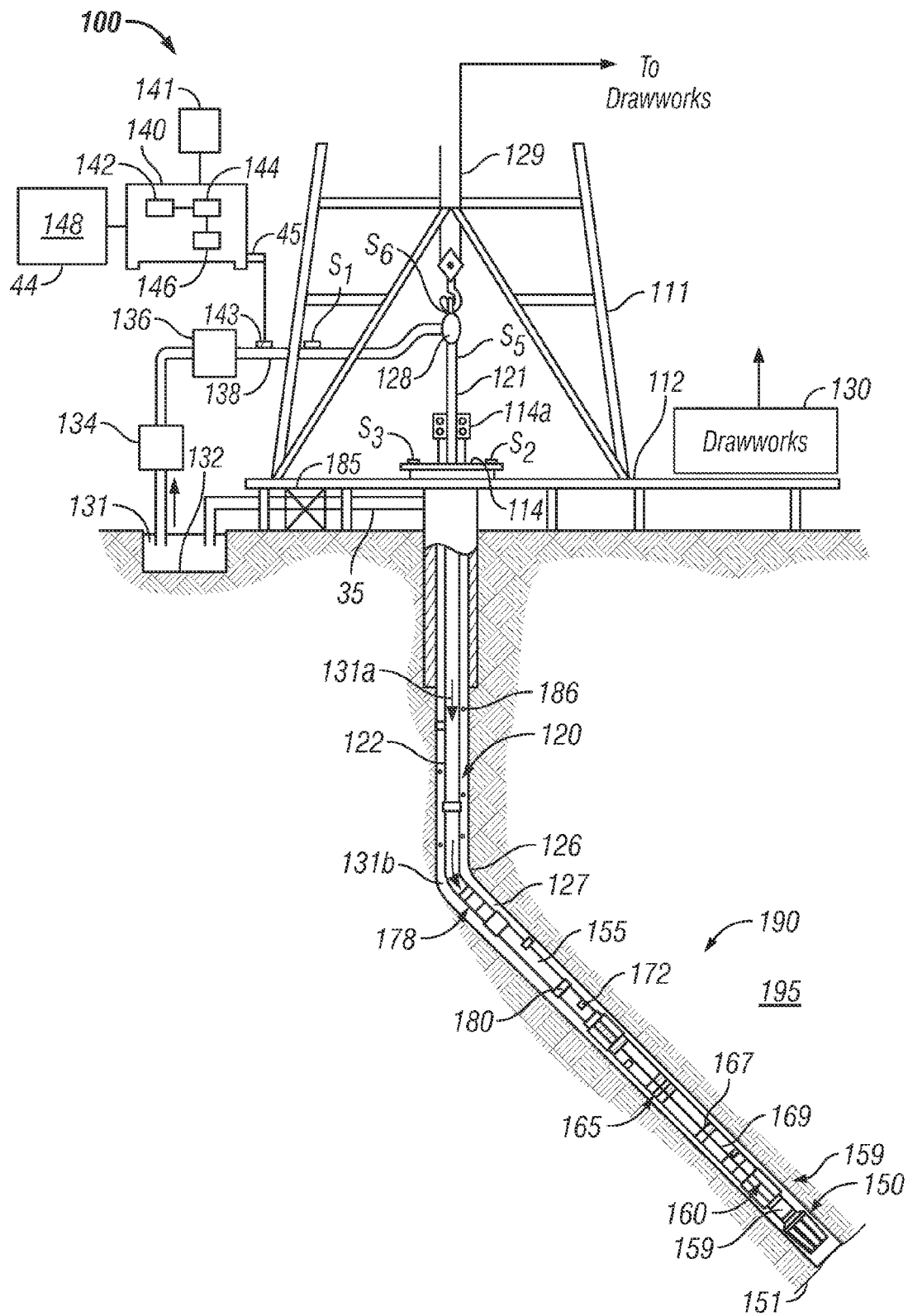
FIG. 1 is a schematic diagram of an exemplary drilling system that includes a drill string having a drilling assembly attached to its bottom end that can be operated according to the exemplary methods apparatus disclosed herein.

FIG. 1 is a schematic diagram of an exemplary drilling system 100 that includes a drill string having a drilling assembly attached to its bottom end that can be operated according to the exemplary methods apparatus disclosed herein. FIG. 1 shows a drill string 120 that includes a drilling assembly or bottomhole assembly ("BHA") 190 conveyed in a wellbore 126. The drilling system 100 includes a conventional derrick 111 erected on a platform or floor 112 which supports a rotary table 114 that is rotated by a prime mover, such as an electric motor (not shown), at a desired rotational speed. A tubing (such as jointed drill pipe) 122 having the drilling assembly 190 attached at its bottom end extends from the surface to the bottom 151 of the wellbore 126. A drill bit 150, attached to drilling assembly 190, disintegrates the geological formations when it is rotated to drill the wellbore 126. The drill string 120 is coupled to a drawworks 130 via a Kelly joint 121, swivel 128 and line 129 through a pulley. Drawworks 130 is operated to control the weight on bit ("WOB"). The drill string 120 can be rotated by a top drive (not shown) instead of by the prime mover and the rotary table 114. The operation of the drawworks 130 is known in the art and is thus not described in detail herein.

In an aspect, a suitable drilling fluid 131 (also referred to as "mud") from a source 132 thereof, such as a mud pit, is circulated under pressure through the drill string 120 by a mud pump 134. The drilling fluid 131 passes from the mud pump 134 into the drill string 120 via a de-surger 136 and the fluid line 138. The drilling fluid 131a from the drilling tubular discharges at the wellbore bottom 151 through openings in the drill bit 150. The returning drilling fluid 131b circulates uphole through the annular space 127 between the drill string 120 and the wellbore 126 and returns to the mud pit 132 via a return line 135 and drill cutting screen 185 that removes the drill cuttings 186 from the returning drilling fluid 131b. A sensor $S_1$ in line 138 provides information about the fluid flow rate. A surface torque sensor $S_2$ and a sensor $S_3$ associated with the drill string 120 provide information about the torque and the rotational speed of the drill string 120. Rate of penetration of the drill string 120 can be determined from the sensor $S_5$, while the sensor $S_6$ can provide the hook load of the drill string 120.

In some applications, the drill bit 150 is rotated by rotating the drill pipe 122. However, in other applications, a downhole motor 155 (mud motor) disposed in the drilling assembly 190 also rotates the drill bit 150. The rate of penetration ("ROP") for a given drill bit and BHA largely depends on the WOB or the thrust force on the drill bit 150 and its rotational speed.

A surface control unit or controller 140 receives signals from downhole sensors and devices via a sensor 143 placed in the fluid line 138 and signals from sensors $S_1$-$S_6$ and other sensors used in the system 100 and processes such signals according to programmed instructions provided from a program to the surface control unit 140. The surface control unit 140 displays desired drilling parameters and other information on a display/monitor 141 that is utilized by an operator to control the drilling operations. The surface control unit 140 can be a computer-based unit that can include a processor 142 (such as a microprocessor), a storage device 144, such as a solid-state memory, tape or hard disc, and one or more computer programs 146 in the storage device 144 that are accessible to the processor 142 for executing instructions contained in such programs to perform the methods disclosed herein. The surface control unit 140 can further communicate with a remote control unit 148. The surface control unit 140 can process data relating to the drilling operations, data from the sensors and devices on the surface, and data received from downhole and can control one or more operations of the downhole and surface devices. Alternately, the methods disclosed herein can be performed at a downhole processor 172.

The drilling assembly 190 also contains formation evaluation sensors or devices (also referred to as measurement-while-drilling, "MWD," or logging-while-drilling, "LWD," sensors) determining resistivity, density, porosity, permeability, acoustic properties, nuclear-magnetic resonance properties, corrosive properties of the fluids or formation downhole, salt or saline content, and other selected properties of the formation 195 surrounding the drilling assembly 190. Such sensors are generally known in the art and for convenience are generally denoted herein by numeral 165. The drilling assembly 190 also includes one or more RHMDs 167 for estimating rock strength of a formation according to the exemplary methods disclosed herein. The drilling assembly 190 can further include a variety of other sensors and communication devices 159 for controlling and/or determining one or more functions and properties of the drilling assembly (such as velocity, vibration, bending moment, acceleration, oscillations, whirl, stick-slip, etc.) and drilling operating parameters, such as weight-on-bit, fluid flow rate, pressure, temperature, rate of penetration, azimuth, tool face, drill bit rotation, etc. In addition, the drilling assembly 190 can also include one or more accelerometers 169 or equivalent devices for estimating an orientation of the drill string and of the one or more rock hardness measurement devices (RHMD) 167 in the wellbore. A suitable telemetry sub 180 using, for example, two-way telemetry, is also provided as illustrated in the drilling assembly 190 and provides information from the various sensors and to the surface control unit 140.

Still referring to FIG. 1, the drill string 120 further includes energy conversion device 160. In an aspect, the energy conversion device 160 is located in the BHA 190 to provide an electrical power or energy, such as current, to sensors 165, RHMD 167 and/or communication devices 159. Energy conversion device 160 can include a battery or an energy conversion device that can for example convert or harvest energy from pressure waves of drilling mud which are received by and flow through the drill string 120 and BHA 190. Alternately, a power source at the surface can be used to power the various equipment downhole.

Figure 2:
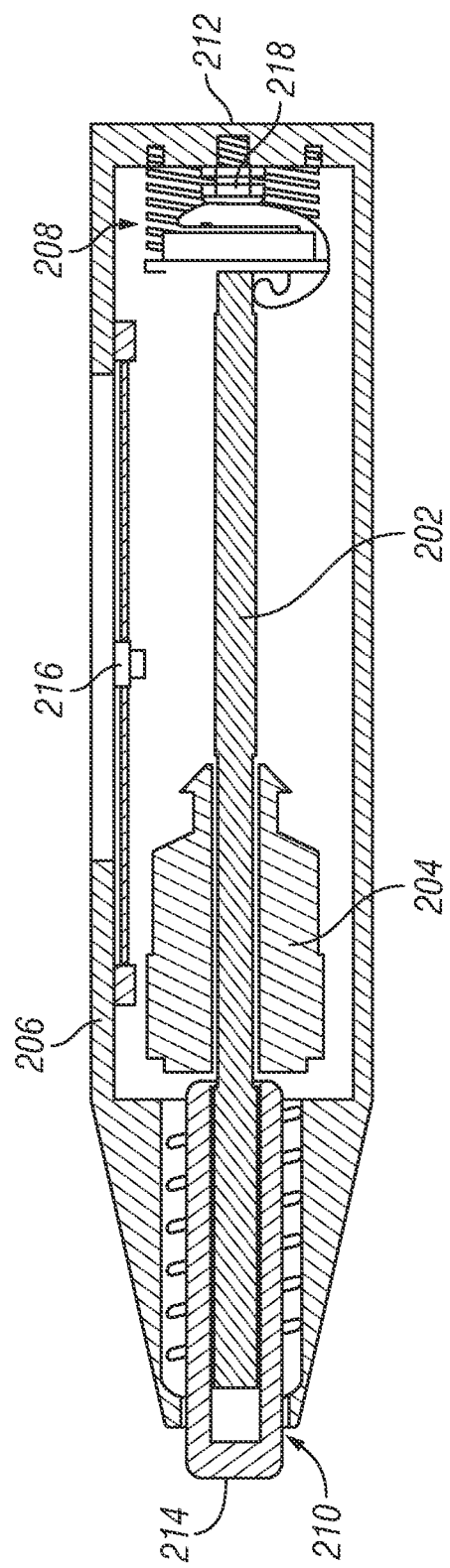
FIG. 2 shows an exemplary rock hardness measurement device (RHMD) suitable for use in the exemplary system of the present disclosure.

FIG. 2 shows an exemplary rock hardness measurement device (RHMD) 167 suitable for use in the exemplary system of the present disclosure. In an exemplary embodiment, the RHMD is a Schmidt Hammer tool known in the art for non-destructive testing and for measuring strength of various structures such as bridges, dams, foundation, etc. The exemplary RHMD 167 includes a piston 202 with an affixed hammer mass 204. The piston is configured to slide in and out of casing 206 through opening 210 at one end of the RHMD. The piston can reside in a retracted position within the casing 206 by compressing the compression spring 208 against end 212 of the RHMD opposite the opening 210. The piston and compression spring are held in the retracted position by a trip screw 218 in a first position. The trip screw 218 moves from the first position to a second position to release the compression spring, which upon being released propels the piston 202 outward from opening 210. The RHMD 167 in one aspect propels the piston 202 at a surface of a test material. Piston 202 has a tip 214 having a surface configured to impact and rebound from the test material. The amount of rebound of the piston/tip from the test material is measured to obtain the hardness of the test material. In one aspect, rebound measuring unit 216 obtains a measure of the rebound and creates an electronic or digital signal indicating the measured rebound and/or the hardness of the material. The created signal can be sent to a processor coupled to the RHMD 167. The processor can use the measured hardness of the material to estimate rock strength of the tested material. In various embodiments, the RHMD 167 includes means for resetting the piston in its retracted position and thus can be used at a downhole remote location from an operator.

Figure 3A:
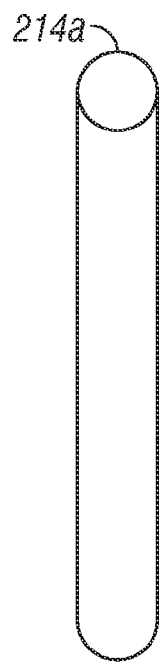
FIG. 3A shows a typical piston tip used in obtaining rock hardness measurements.
Figure 3B:
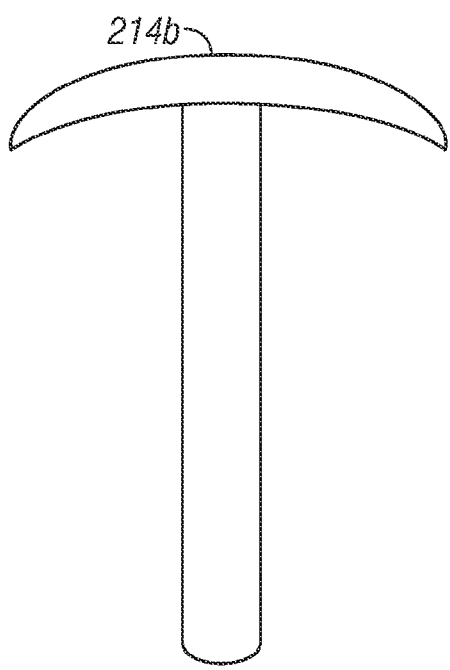
FIG. 3B shows an exemplary piston tip suitable for use in obtaining rock hardness measurements in a wellbore.

In one embodiment, the tip is configured to obtain a hardness measurement in a wellbore. FIG. 3A shows a typical piston tip 214a used in rock hardness testing. Tip 214a is typically a surface of a hemisphere having a diameter of approximately 1 cm. However, wellbore surfaces can be rough due to natural rock surfaces, washout and other forces. Therefore, the tip 214a of FIG. 3A can slip along the wellbore surface or otherwise poorly impact the wellbore surface. The present disclosure therefore provides a piston having a tip 214b (FIG. 3B) configured to impact the wellbore surface without slipping. In one embodiment, tip 214b is a surface of a sphere having a radius of curvature of approximately 10 cm. Tip 214b is therefore able to impact a rough surface and not slip against it. The geometry of the tip enables acquisition of the rebound hardness number in mud cake zones, highly fractured zones and highly weather areas. In addition, tip 214b is applicable on rough or curved wellbore surfaces having dented or concaved irregularities.

Figure 4A:
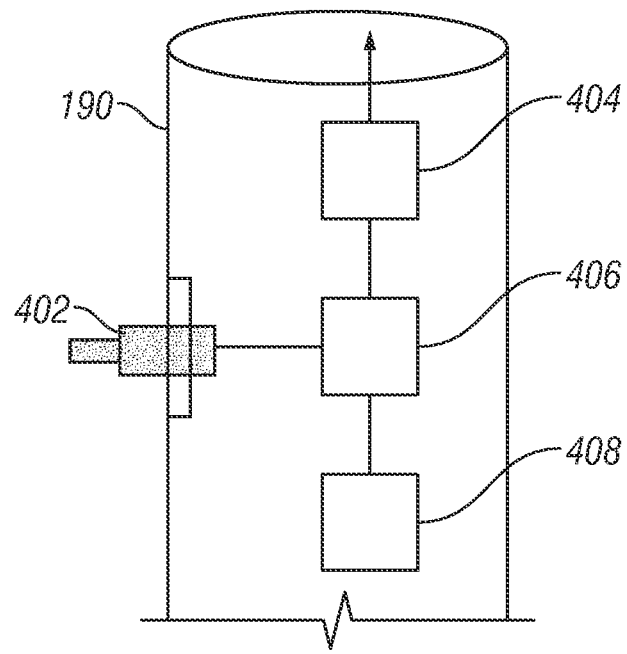
FIG. 4A shows a section of a downhole tool having an exemplary downhole RHMD according to one embodiment of the present disclosure.

FIG. 4A shows a section of a downhole tool 190 having an exemplary downhole RHMD 402 according to one embodiment of the present disclosure, such as the RHMD of FIG. 2. The RHMD 402 is conveyed downhole with bottomhole assembly and pressed against a surface of the wellbore. The RHMD is activated to propel the piston and tip against the wellbore surface to thereby obtain a rock hardness measurement. RHMD 402 is coupled to processor 406, which can receive the obtained rock hardness measurement from the RHMD and estimate rock strength of the formation at the location. Additionally, a rock strength profile can be estimated at processor 406. An orientation device 408 provides orientation of the drill string and/or RHMD to processor 406. Orientation of the RHMD affects the measurements obtained of rock hardness. For example, a horizontal placement of the RHMD wherein the piston is propelled horizontally is substantially unaffected by gravitational force. However, if the piston is propelled in a direction that has a vertical component (i.e., vertical direction), the gravitational force affects the acceleration of the piston and therefore the impact of the piston has against a material to be tested. If the RHMD is oriented so that the piston is propelled downward to the test surface, the piston impacts the test surface with more energy. If the RHMD is oriented so that the piston is propelled upward to the test surface, the piston impacts the test surface with less energy. Processor 406 therefore computes rock strength using the obtained hardness measurements from the RHMD 402 and an orientation of the RHMD 402, as discussed below with respect to FIG. 5. In one embodiment, computed rock strength can be sent to a surface location using telemetry device 204 for calculations at surface control unit 140.

Figure 4B:
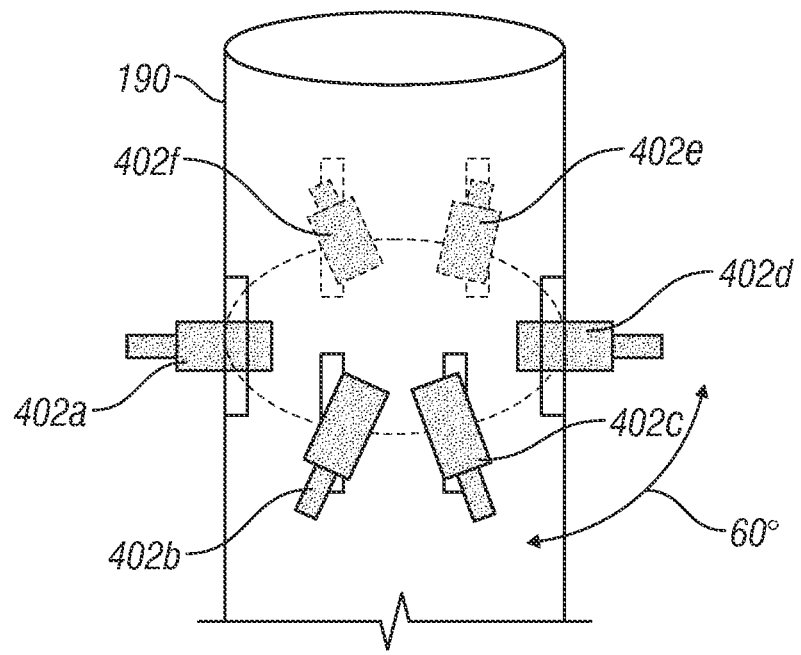
FIG. 4B shows another exemplary embodiment of the present disclosure which includes a plurality of RHMDs circumferentially spaced about the tool.

FIG. 4B shows another exemplary embodiment of the present disclosure which includes a plurality of RHMDs 402a-402f circumferentially spaced about the tool 190. Although six RHMDs are shown for illustrative purposes, the number of RHMDs is not meant as a limitation of the present disclosure. Referring to FIG. 2B, six exemplary RHMDs are spaced at 60° along the circumference of tool 190. The circumferentially-spaced RHMDs 402a-402f enable an operator to obtain measurements of rock hardness at various azimuthal locations around the tool. In an alternate method of obtaining rock hardness measurements at a plurality of azimuthal locations, the single RHMD 402 of FIG. 4A can be rotated to the circumferential positions of RHMDs 402a-402f and activated to obtain measurements at each location. Both tools of FIG. 2A and FIG. 2B can be moved axially to obtain hardness measurements at a plurality of depths of the wellbore. The hardness measurements at the plurality of depths can be used to obtain a rock strength profile of the formation. Typically hardness measurements are obtained at various depths of the wellbore. The rock strength profile can be measured at a single azimuthal location or can be measured at a plurality of azimuthal locations to obtain two- and three-dimensional rock strength profiles.

In various embodiments, the exemplary RHMDs obtain measurements at a particular location in the wellbore by obtaining multiple measurements at the location and nearby locations and averaging values. A maximum and minimum measurement at the particular location may be disregarded and an average taken of the remaining values. Impacting the wellbore formation at the particular location generally affects subsequent rock hardness measurements. Therefore, subsequent measurements related to the particular location can be obtained by moving the RHMD device to a nearby location which may be at a distance of between 10 cm and 30 cm.

In one embodiment, the RHMDs of FIGS. 4A and 4B are conveyed within a compartment within tool 190 to the downhole location and are extended from the compartment to obtain rock hardness measurements. In another aspect, the RHMDs are conveyed on pads coupled to tool 190. The pads can be extended from the tool to abut the RHMDs against the wellbore to obtain rock hardness measurements. Although not shown in FIG. 4B, RHMDs 402a-402f can be coupled to one or more orientation devices for estimating orientations of the RHMDs and to a processor for estimating rock strength from obtained rock hardness measurements and orientation measurements. Also, a telemetry device can provide estimated values to a surface location.

Figure 5:
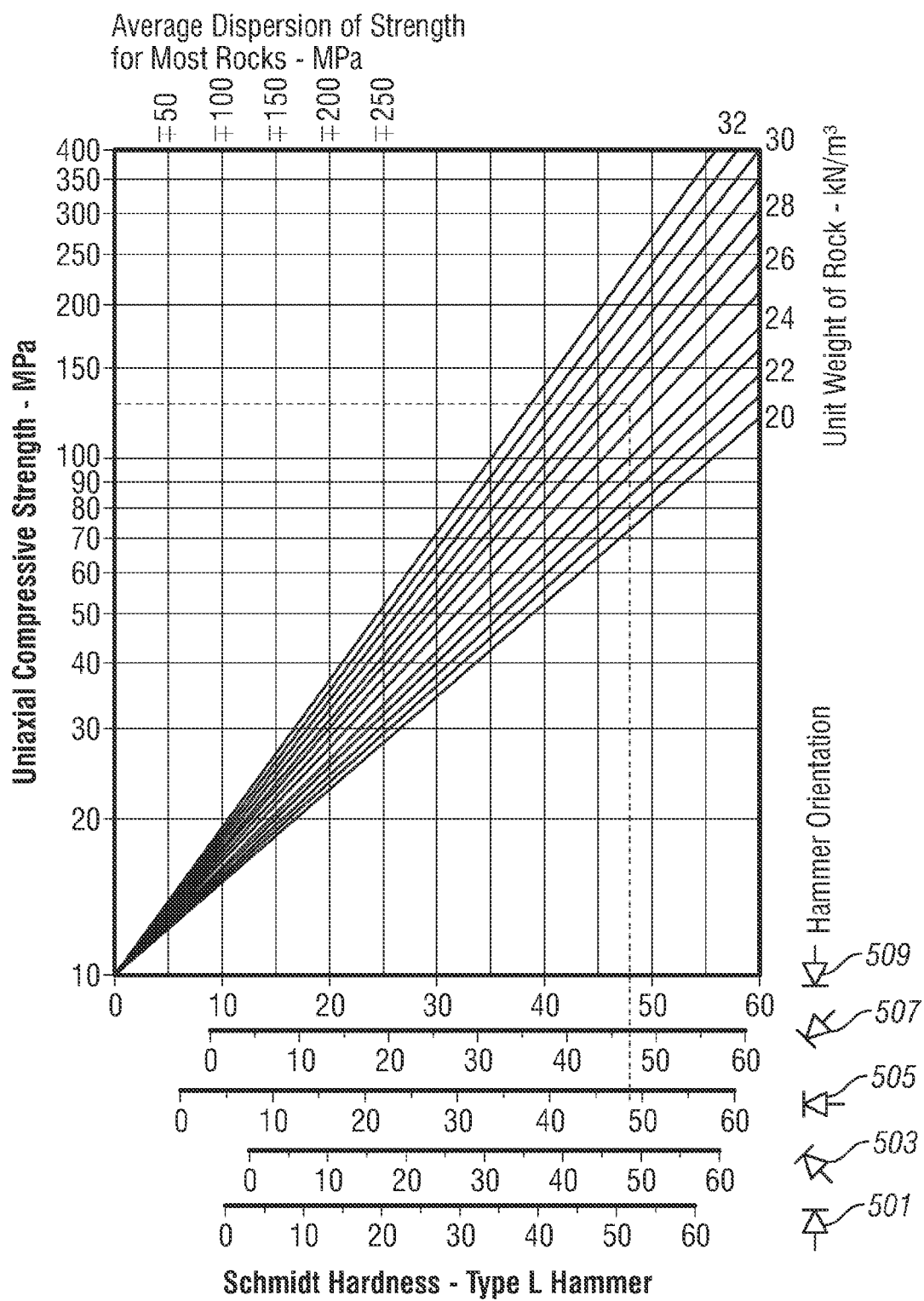
FIG. 5 shows an exemplary chart suitable for estimating rock strength of a formation using hardness measurements obtained at a downhole location.

FIG. 5 shows an exemplary chart 500 for estimating rock strength of a formation using hardness measurements obtained at a downhole location. Multiple rock hardness scales 501, 503, 505, 507 and 509 are shown along an x-axis.

Each rock hardness scale corresponds to an orientation of an RHMD. Hence, scale 501 corresponds to a RHMD in a vertical orientation with the piston directed to be propelled downward. Scale 503 corresponds to the RHMD orientated at 45° to the downward vertical direction. Scale 505 corresponds to the RHMD oriented horizontally. Scale 507 corresponds to the RHMD oriented at 45° to an upward vertical direction. Scale 509 corresponds to the RHMD oriented vertically with the piston directed to be propelled upward. Uniaxial compressive strength (rock strength) is shown along the y-axis in MegaPascals. A plurality of rock density lines are shown along chart 500. Each rock density lines is related to density of various rock types, such as dolomite, granite, sandstone, shale rock, for example. Rock strength is estimated using an appropriate rock hardness scale and rock density. For example, a rock hardness of 48 is obtained at a RHMD which is oriented in a horizontal direction and for which the density of rock is 26 kN/m$^3$. Rock density can be estimated using various methods such as acoustic measurements and/or gamma ray measurements. Therefore, the number 48 is located on scale 505, which applied to a horizontally directed piston. Using the rock density line labeled 26 in FIG. 5, the rock strength is estimated to be about 140 MPa.

In various aspects, the obtained rock strength profile can be used to characterize in-situ wellbore stress conditions in real-time. The methods and apparatus can be used as part of a measurement-while-drilling device or in wireline logging and drilling parameters can be altered based on the rock strength profile. In general, sedimentary reservoir formations show high anisotropic effects because of several fracture networks such as bedding planes, joints, laminations, etc. Therefore, multiple orientations of rebound hardness measurements provide an improved measurement of wellbore strength compared to a single alignment of a rebound hardness measurement.

Therefore, in one aspect, the present disclosure provides a method of estimating a rock strength profile of a formation, the method including: conveying a tool having a testing surface into a wellbore in the formation; propelling the testing surface to impact the formation at a plurality of depths in the wellbore; obtaining a measurement of hardness of the formation from a rebound of the testing surface from the formation at the plurality of depths; and estimating the rock strength profile of the formation using the obtained measurements of hardness at the plurality of depths. A parameter for drilling the wellbore can be affected or altered using the estimated rock strength profile. In one embodiment, the testing surface is configured to rebound from at least one of: (i) washout zone of the formation; (ii) a rough surface of the formation; (iii) a mud cake on the formation. Measurements of hardness of the formation can be obtained at a plurality of azimuthal locations. In one embodiment, the measurements can be obtained by one of: (i) rotating the tool having a single testing surface to obtain hardness measurements at the plurality of circumference locations; and (ii) obtaining the hardness measurements at a plurality of testing surfaces located at selected azimuthal locations of the tool. Rock hardness measurements can be obtained using at least one of: (i) spaced testing surfaces at separate axial locations of the tool; and (ii) radially spaced testing surfaces. An orientation of the testing surface in the wellbore can be obtained with respect to one of a: (i) vertical direction, and (ii) horizontal direction, and the rock strength estimated using the obtained measurement of rock hardness and the estimated orientation. The downhole tool can be used on a drill string or on a wireline. Hardness measurements can be obtained at axially separated depths of the wellbore and an average hardness measurement can be obtained using the axially separated hardness measurements.

In another aspect, the present disclosure provides a method of drilling a wellbore, the method including: conveying a tool having a testing surface into a wellbore in the formation; propelling the testing surface to impact the formation at a plurality of depths in the wellbore; obtaining a measurement of hardness of the formation from a rebound of the testing surface from the formation at the plurality of depths; estimating the rock strength profile of the formation using the obtained measurements of hardness at the plurality of depths; and affecting a parameter for drilling the wellbore using the estimated rock strength profile.

In another aspect, the present disclosure provides an apparatus for estimating a rock strength profile of a formation, comprising: a tool configured to be conveyed into the wellbore; a testing surface disposed on the tool configured to propel against the formation at a plurality of depths in the wellbore and rebound from the formation as a result of the impact; and a processor configured to: obtain a measurement of hardness of the formation from a rebound of the testing surface from the formation at the plurality of depths, and estimate the rock strength profile of the formation from the obtained measurements of hardness at the plurality of depths. The processor can be further configured to affect a parameter for drilling the wellbore using the estimated rock strength profile. The testing surface can be configured to impact at least one of: (i) a washout zone of the formation; (ii) a rough surface of the formation; (iii) a mud cake on the formation. The apparatus can in one embodiment include a plurality of testing surfaces azimuthally spaced around the tool. The apparatus can in another embodiment include the tool having a single testing surface configured to rotate to the plurality of azimuthal locations to obtain the measurement of hardness of the formation at the plurality of azimuthal locations. The testing surface can be at least one of (i) testing surfaces at separate axial locations of the tool; and (ii) radially spaced testing surfaces. In one embodiment, an orientation sensor is configured to estimate an orientation of the testing surface in the wellbore and the processor is configured to estimate the rock strength using the obtained hardness measurement and the estimated orientation. The apparatus can be conveyed in the wellbore on either a drill string or a wireline. The processor can be further configured to obtain an average of hardness measurements obtained at axially separated depths.

While the foregoing disclosure is directed to the preferred embodiments of the disclosure, various modifications will be apparent to those skilled in the art. It is intended that all variations within the scope and spirit of the appended claims be embraced by the foregoing disclosure.

What is claimed is:

1. A method of estimating a rock strength profile of a formation, comprising:
   conveying a tool having a testing surface into a wellbore in the formation;
   determining an orientation of the testing surface using an orientation sensor conveyed downhole;
   propelling the testing surface along a selected direction corresponding to the determined orientation to impact the formation, wherein an energy of impact of the testing surface against the formation is affected by a component of gravitational force along the selected direction;
   obtaining a measurement of hardness of the formation under in-situ stress conditions from a rebound of the testing surface from the formation;
   selecting a hardness scale for the determined orientation of the testing surface;
   measuring a rock density of the formation using a downhole sensor;
   selecting a relationship between the selected rock hardness scale and rock strength for the measured rock density; and
   determining a rock strength of the formation indicated by the measurement of hardness using the selected hardness scale and the relationship between the selected rock hardness scale and rock strength.

2. The method of claim 1 further comprising affecting a parameter for drilling the wellbore using the rock strength.

3. The method of claim 1, wherein the testing surface is configured to rebound from at least one of: (i) a washout zone of the formation; (ii) a rough surface of the formation; (iii) a mud cake zone of the formation.

4. The method of claim 1 further comprising obtaining hardness measurements using at least one of: (i) spaced testing surfaces at separate axial locations of the tool; and (ii) radially spaced testing surfaces.

5. The method of claim 1 further comprising conveying the tool downhole using one of: (i) a drill string; and (ii) a wireline.

6. The method of claim 1 further comprising obtaining measurements of hardness at axially separated depths of the wellbore.

7. The method of claim 6 further comprising obtaining an average hardness measurement from the obtained measurements at axially separated depths.

8. The method of claim 1, wherein the testing surface is configured to impact a rough surface of the formation without slipping.

9. The method of claim 8, wherein the testing surface is a surface having a radius of curvature of about 10 centimeters.

10. The method of claim 1, further comprising obtaining a three-dimensional rock strength profile of the formation.

11. A method of drilling a wellbore, comprising:
    conveying a tool having a testing surface, an orientation sensor and a rock density sensor into a wellbore in the formation;
    determining an orientation of the testing surface using the orientation sensor;
    propelling the testing surface in a selected direction corresponding to the determined orientation to impact the formation, wherein an energy of impact of the testing surface against the formation is affected by a component of gravitational force along the selected direction;
    determining the rock density of the formation using the rock density sensor;
    using a processor to:
      select a hardness scale for the determined orientation,
      measure a rock density of the formation using a downhole sensor,
      select a linear relationship between the selected rock hardness scale and rock strength for the measured rock density, and
      determine a rock strength of the formation indicated by the measurement of hardness using the selected hardness scale and the relationship between the selected rock hardness scale and rock strength, and
      affect a parameter for drilling the wellbore using the estimated rock strength.

12. An apparatus for estimating a rock strength of a formation, comprising:
    a tool configured to be conveyed into the wellbore;
    a testing surface disposed on the tool configured to propel against the formation in a selected direction and rebound from the formation, wherein an energy of impact of the testing surface against the formation is affected by a component of gravitational force along the selected direction; and an orientation sensor disposed on the tool configured to determine an orientation of the tool in the wellbore;

a rock density sensor disposed on the tool;

a processor configured to:
- obtain a measurement of hardness of the formation under in-situ stress conditions from a rebound of the testing surface from the formation,
- obtain the orientation of the tool from the orientation sensor,
- obtain the rock density of the formation from the rock density sensor,
- select a hardness scale for the determined orientation,
- measure a rock density of the formation using a downhole sensor,
- select a linear relationship between the selected rock hardness scale and rock strength for the measured rock density, and
- determine a rock strength of the formation indicated by the measurement of hardness using the selected hardness scale and the relationship between the selected rock hardness scale and rock strength.

13. The apparatus of claim 12, wherein the processor is further configured to affect a parameter for drilling the wellbore using the rock strength.

14. The apparatus of claim 12, wherein the testing surface is configured to rebound from at least one of: (i) a washout zone of the formation; (ii) a rough surface of the formation; (iii) a mud cake zone of the formation.

15. The apparatus of claim 12, wherein the testing surface further comprises at least one of: (i) testing surfaces at separate axial locations of the tool; and (ii) radially spaced testing surfaces.

16. The apparatus of claim 12, wherein the tool further comprising one of: (i) a drill string; and (ii) a wireline.

17. The apparatus of claim 12, wherein the processor further configured to obtain an average of hardness measurements obtained at axially separated depths.

* * * * *